United States Patent [19]

Voelger et al.

[11] 4,118,492

[45] Oct. 3, 1978

[54] DIURETIC PHARMACEUTICAL COMPOSITIONS AND METHOD OF USE CONTAINING THE SULFURIC ACID HALF-ESTER OF 2,4,7-TRIAMINO-6P-HYDROXYPHENYL PTERIDINE

[75] Inventors: Karl-Dieter Voelger, Darmstadt; Christian Rietzel, Heidelberg; Klaus Lehmann, Rossdorf, all of Fed. Rep. of Germany

[73] Assignee: Rohm GmbH, Darmstadt, Fed. Rep. of Germany

[21] Appl. No.: 783,386

[22] Filed: Mar. 31, 1977

[30] Foreign Application Priority Data

Apr. 6, 1976 [DE] Fed. Rep. of Germany ....... 2614738

[51] Int. Cl.² .......................................... A61K 31/505
[52] U.S. Cl. .................................................. 424/251
[58] Field of Search ...................................... 424/251

[56] References Cited

U.S. PATENT DOCUMENTS 3,081,230  3/1963  Weinstock et al. .............. 424/251 X Primary Examiner—Stanley J. Friedman
Attorney, Agent, or Firm—Curtis, Morris & Safford

[57] ABSTRACT

A pharmaceutical composition for inducing diuresis, which composition comprises a diuretically-effective amount of the sulfuric acid half ester of 2,4,7-triamino-6-p-hydroxyphenyl pteridine or of a physiologically tolerable salt thereof in combination with a pharmaceutical carrier.

3 Claims, No Drawings

DIURETIC PHARMACEUTICAL COMPOSITIONS AND METHOD OF USE CONTAINING THE SULFURIC ACID HALF-ESTER OF 2,4,7-TRIAMINO-6P-HYDROXYPHENYL PTERIDINE

DIURETIC PHARMACEUTICAL COMPOSITIONS

The present invention relates to diuretic pharmaceutical compositions containing as the active ingredient the sulfuric acid half-ester of 2,4,7-triamino-6-p-hydroxyphenyl-pteridine or a physiologically tolerable water-soluble salt thereof, which compositions show a sufficient solubility that they may, if desired, by injected as a solution.

The diuretic effect of 2,4,7-triamino-6-phenyl-pteridine—herein after also characterized as "triamterene"— is known and ultilized therapeutically. The disadvantage of this compound is its small solubility so that the administration of pharmaceutical compositions containing this agent has heretofore been limited to oral administration. In emergency situations, thus, the aforementioned pharmaceutical compositions were not utilizable. Attempts to convert the active agent into a soluble, and thereby injectable, form have heretofore been unsuccessful.

Triamterene belongs to the group of potassiumretaining diuretics. Details over the manner in which Triamterene is effective are known from model tests on the main excretory duct of the salivary glands of rats. This glandular duct was chosen as a model since the epithelium thereof transports $Na^+$, $K^+$, and $H^+/HCO_3^-$ in the same way as does the distal tubule of the kidney. [Knauf et al., Pfluegers Arch., 333, 82–94 (1972); 361, 55 (1975)]. The works of Knauf and others have shown that a complete inhibition of $Na^+$ back-resorption is attained with $10^{-4}$ M of Triamteren and that $K^+$ secretion decreases to half of its initial value. [Europ. J. clin. Invest. 6, 43–50 (1976)].

These changes in electrolyte transport are caused by an inhibition of the $Na^+$ inflow from the lumen into the cells, as can be determined from measurements of permeability. Since the $Na^+$ inflow is functionally coupled with the outflow of $K^+$, its blockade has as a consequence an inhibition of $K^+$ secretion so that the potassium loss connected with nearly all diuretics is extensively hindered by treatment with triamterene. In the test carried out by Knauf et al., use is made of the microperfusion technique described by Young et al. [Pfluegers Arch. 295, 157 (1967)].

The effect of triamterene is evident in the aforementioned research method from the decrease of the difference in electric potential between the lumen and the interstitium, which is a measure of the $Na^+$ transport. The inhibitory effect can only be achieved outwardly from the lumen side, since even the highest doses of triamterene in a bath solution surrounding the isolated gland duct, i.e. from the blood side, are ineffective. The concepts concerning the mechanism of operation of triamterene, supported by the results of the aforementioned measuring techniques, can be viewed as certain. In attacking the problem which was to be solved by the present invention, namely to convert triamterene into a soluble and thereby injectable form while retaining the same diuretic and potassium-retaining effect, use could be made of the reliable investigatory methods worked out for the testing of triamterene.

It was obvious to investigate the metabolic products of triamterene excreted by the kidneys, that is, therefore, soluble metabolic products, for their diuretic effect. In 1965, Lebmann reported in "Arzneimittelforschung", 15 (7), 812–816 concerning the separation, isolation, and identification of the metabolic products of triamterene. According to this report, 2,4,7-triamino-6-p-hydroxyphenyl-pteridine was itself excreted in a small amount in addition to unchanged triamterene and the sulfuric acid ester of 2,4,7-triamino-6-p-hydroxyphenyl-pteridine. Weinstock et al. in 1968 reported on the diuretic efficacy of derivatives of 2,4,7-triamino-6-phenyl-pteridine [J. Med. Chem. 11, 573–579 (1968)] and determined that the p-hydroxy analog of triamterene, one of the metabolities of this compound, shows no diuretic effect. Those of the triamterene derivatives tested, which have any diuretic effect at all are according to Weinstock's investigations compounds having apolar substituents, for example the p-toluyl-homolog of triamterene. Derivatives having polar groups, for example with an amino or nitro group, are —in contrast— diuretically inactive. (op. cit. Table VIII).

In view of this discovery, it could not be expected that the sulfuric acid half-ester of the diuretically-inactive "p-hydroxy-triamterene", i.e. a triamterene derivative with a polar group, would show diuretic activity.

It has now been found that, surprisingly, the sulfuric acid half-ester of 2,4,7-triamino-6-p-hydroxyphenyl-pteridine shows practically the same efficacy as triamterene not only from the viewpoint of urea excreting activity but also from the point of view of potassium retention, but is nevertheless superior to triamterene because of the solubility of many physiologically tolerable salts, particularly the alkali metal salts, of the aforementioned sulfuric acid ester. The solubility of the sulfuric acid half-ester of 2,4,7-triamino-6-p-hydroxyphenyl-pteridine is sufficient to permit injection of this agent. Oral administration of the drug of the invention is less suitable, but compositions for such oral administration are contemplated herein as part of the desired protection. In case of oral administration, the compositions and dosages conventionally used with triamterene are suitable also for the agent of the present invention.

The aforementioned sulfuric acid half-ester can be prepared in the following way.

124 mg of dicyclohexylcarbodiimide were dissolved in 0.2 ml of dimethylformamide dried over a molecular sieve (4A). A clear solution of 32 mg of 2,4,7-triamino-6-p-hydroxyphenyl-pteridine in 0.7 ml of dry hexamethylphosphoric acid triamide (dried over a molecular sieve 10A), prepared by dissolving at boiling temperature and cooling to room temperature, was added to this solution.

0.5 ml of 96% sulfuric acid was brought to a volume of 10 ml with ice-cold dry dimethylformamide with ice-cooling. The dicyclohexylcarbodiimide/2,4,7-triamino-6p-hydroxyphenyl-pteridine solution was now immediately combined, with ice cooling, with 0.15 ml of the cold $H_2SO_4$/dimethylformamide solution. After several minutes, the reaction mixture became cloudy; dicyclohexylurea precipitated.

After 30 minutes, the mixture was diluted with 25 ml of dry dimethylformamide and neutralized with ice-cooling with 1 N NaOH. The precipitated dicyclohexylurea was filtered off using a G 3-frit and the filtrate was reduced in an oil pump vacuum at a bath temperature of 30° C. Since the hexamethylphosphoric acid triamide still did not come over at this temperature, the residue was combined with ether and the precipitate was centrifuged off. After decanting off the clear residue, it was dissolved in 0.5 ml of 1 N ammonia and 1 ml of dimethylsulfoxide and diluted with 20 ml of 0.01 M pyridinium acetate solution. The clear yellow solution was chromatographed on DEAE-Sephadex A 25 (acetate form; column = 3 × 23 cm) which was equilibrated with 0.01 M pyridinium acetate solution. Unconverted hydroxy compound was eluted immediately, whereas the sulfuric acid ester came off only after applying a gradient against 1 M pyridinium acetate solution. The course of elution was followed by measurement of the extinction of the individual fractions at 365 nm with a photometer. After thin-layer chromatographic identification, the eluate containing sulfuric acid was evaporated to dryness in an oil pump vacuum at 30° C. The residue was taken up in a little 1 N ammonia and the filtered solution was brought to a pH of 5–6 with a few drops of glacial acetic acid. On keeping the solution in a refrigerator, the sulfuric acid half-ester crystallized out.

Yield: 12 mg (29% of theory) Thin-layer chromatographic purity control (solvent system: $CHCl_3$-methanol-water, 65:35:4): uniform.

The compound of the present invention is preferably administered parenterally, above all intravenously, in the form of a solution thereof or of a physiologically-tolerable soluble salt. Such salts include alkali metal salts, such as of sodium and potassium, ammonium salts, substituted ammonium salts such as the lower trialkyl amine salts, salts of N-lower alkyl piperidines, of procain, alkanolamines, choline, etc. For parenteral, particularly intravenous administration, such amounts of the active ingredient or of its salts is given such that concentration of drug in the plasma of normal persons can be up to 20 mg, and up to 5 mg for special plasma concentrations.

A medicament for intravenous administration can be prepared as follows.

500 mg of the sulfuric acid half ester of 2,4,7-triamino-6-hydroxyphenyl-pteridine is introduced with stirring into a solution of 1g of triethylamine and 1 ml of water (suitable for injection). The mixture is diluted to 10 ml with water suitable for injection, and filtered through a fine-pored filter for germ removal and removal of any solid matter. The content of active material was then determined under aseptic conditions. Samples were adjusted with water for injection purposes to a content of about 5 mg/ml, then with HCl in water for injection purposes to a pH of 9, and finally diluted with water to the calculated volume. The solution was filled into ampoules under sterile conditions.

For parenteral (intravenous) administration, a sufficient stability of the active agent is a requirement. The stability of the agent to hydrolysis was determined below by measurement of its distribution between lipophilic and aqueous phases. The measurement at the same time gives an indication of the hydrophilicity of the compound.

(1) Determination of the stability of hydrolysis

Because the distribution coefficient must be altered upon hydrolysis of the ester, the stability of the sulfuric acid half ester of 2,4,7-triamino-6-p-hydroxyphenyl-pteridine under hydrolytic conditions can be determined by measurements which follow the distribution of the material between an aqueous phase and a lipophilic phase.

Test procedure: 0.33 mg of the sulfuric acid half ester of 2,4,7-triamino-6-p-hydroxyphenyl-pteridine is dissolved in 10 mM of Tris-HCl-buffer (pH = 7.4) ($10^{-4}$M solution). The aqueous phase, in defined dilution stages, is shaken (equilibrated) with the same volume of n-octanol at constant temperature. After separation of the phases by means of centrifugation, the ester concentration is in each case determined photometrically. As a comparison value, the distribution coefficient of triamterene was measured in parallel.

Results: The distribution coefficient, $p$, for triamterene in the system n-octanol/water = 12.8 at room temperature; the distribution coefficient, $p$, of the ester directly after being put in solution in the same system = 0.029 at room temperature.

After 72 hours storage at room temperature, the distribution quotient of the sulfuric acid half ester remains the same ($p = 0.029$, as the mean value from 10 determinations).

(2) Diuretic Activity

Test procedure: During luminal perfusion of the salivary gland ducts of male rats according to the method described by Knauf et al. [Pflueger's Arch. 316, 238 (1970)], the difference in electric potential was continuously registered. The perfusion solution employed was a solution of 140 mVal $Na^+$ as the sulfate in water, buffered with 10 mM Tris-HCl.

Under these conditions, the potential difference established between the lumen and the interstitium is dependent only on the $Na^+$ - transport. A decrease of the potential difference by triamterene signifies a decrease in the $Na^+$ - transport and, therewith, a diuretic effect.

Results: A perfusion with the sulfuric acid half-ester of 2,4,7-triamino-6-p-hydroxyphenol-pteridine and 2,4,7-triamino-6-phenyl-pteridine (triamterene) as a comparison in a $10^{-4}$ M concentration gives a corresponding decrease in the sodium potential in both cases. The effect is completely reversible.

Determination of the half-maximum inhibition $I_{50}$: The values given in the following table are determined in a sodium sulfate solution of 140 mVal (Tris-buffered at pH = 7.4), as above. The inhibition of the sodium-back resorption is reported as the half-maximum effective dose $I_{50}$.

| Agent | $I_{50}$ |
|---|---|
| 2,4,7-triamino-6-phenyl-pteridine (Triamterene) | $3 \times 10^{-5}$ mol |
| sulfuric acid half ester of 2,4,7-triamino-6-p hydroxyphenyl-pteridine | $8 \times 10^{-5}$ mol |

Summary of the results: The sulfuric acid half ester has, on a molar basis, the same effect on the $Na^+$-potential as triamterene itself. The diuretic effect to be expected from this discovery is confirmed by the transport studies.

(3) Complete inhibition of $Na^+$-transport/investigation of the $K^+$-secretion according to Knauf (loc. cit.)

With a $10^{-4}$ molar concentration of the sulfuric acid half ester in Tyrode solution* (pH = 7.4), $Na^+$-transport is completely blocked. (Decrease from 39 ± 3 to 1.9 ± 3.4 nEq/min., i.e. to a value which is not significantly different from 0). The measurement in each case is done in the same (same sized) excretory duct. For triamterene, the flow was 1.5 nEq/min. per excretory duct.

*Tyrode solution is prepared from the following materials, in parts by weight, in 100 parts by weight of water: 0.8 NaCl; 0.02 KCl; 0.02 CaCl$_2$; 0.01 MgCl$_2$; 0.005 NaH$_2$PO$_4$; 0.1 NaHCO$_3$; 0.1 glucose.

The effect on K$^+$-secretion can be best compared under conditions of the total inhibition of Na$^+$-resorption.

It was found that the sulfuric acid half ester of 2,4,7-triamino-6-p-hydroxyphenyl pteridine is more strongly inhibitory on K$^+$-secretion, that is more K$^+$-ions are retained than with triamterene. The K$^+$-secretion decreases from 27 ± 3 nEq/min. to 4 ± 1 nEq/min. The measurement takes place on the same (same size) excretory duct. For triamterene, the flow was 12 nEq/min. per duct.

What is claimed is:

1. The method of inducing diuresis in a patient requiring the same, which method comprises orally, parenterally, or intravenously administering to said patient a diuretically effective amount of the sulfuric acid half ester of 2,4,7-triamino-6-p-hydroxyphenyl pteridine or of a physiologically tolerable salt thereof.

2. The method as in claim 1, wherein said salt is a water-soluble salt and administration is by the intravenous route.

3. A pharmaceutical composition for inducing diuresis, which composition comprises a diuretically effective amount of a physiologically tolerable water soluble salt of 2,4,7-triamino-6-p-hydroxy-phenylpteridine in combination with an aqueous carrier for injection.

* * * * *

UNITED STATES PATENT AND TRADEMARK OFFICE
CERTIFICATE OF CORRECTION

PATENT NO. : 4,118,492
DATED : October 3, 1978
INVENTOR(S) : Karl-Dieter Voelger et al.

It is certified that error appears in the above-identified patent and that said Letters Patent are hereby corrected as shown below:

Column 6, line 13, after "salt" insert --of the sulfuric acid half ester--.

Signed and Sealed this

Tenth Day of July 1979

[SEAL]

Attest:

Attesting Officer

LUTRELLE F. PARKER
Acting Commissioner of Patents and Trademarks